US009082520B2

(12) United States Patent
Prince et al.

(10) Patent No.: US 9,082,520 B2
(45) Date of Patent: *Jul. 14, 2015

(54) MULTI LEVEL MULTILEAF COLLIMATORS

(71) Applicant: Varian Medical Systems, Inc., Palo Alto, CA (US)

(72) Inventors: Steven W. Prince, San Francisco, CA (US); Stanley Mansfield, Sunnyvale, CA (US)

(73) Assignee: Varian Medical Systems, Inc., Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/144,509

(22) Filed: Dec. 30, 2013

(65) Prior Publication Data

US 2014/0112453 A1 Apr. 24, 2014

Related U.S. Application Data

(63) Continuation of application No. 12/861,368, filed on Aug. 23, 2010, now Pat. No. 8,637,841.

(51) Int. Cl.
*G21F 3/00* (2006.01)
*G21K 1/04* (2006.01)

(52) U.S. Cl.
CPC ..................... *G21K 1/046* (2013.01)

(58) Field of Classification Search
CPC ........... G21K 1/00; G21K 1/02; G21K 1/025; G01N 2223/316; G01N 2223/3301
USPC ............ 250/396 R, 398, 492.1, 492.3, 505.1, 250/515.1, 517.1; 378/145, 147, 148, 149, 378/150, 151, 152, 153
See application file for complete search history.

(56) References Cited

U.S. PATENT DOCUMENTS

| 4,868,844 | A | 9/1989 | Nunan |
|---|---|---|---|
| 4,987,309 | A | 1/1991 | Klasen et al. |
| 5,591,983 | A | 1/1997 | Yao |
| 6,266,393 | B1 | 7/2001 | Ein-Gal |
| 6,526,123 | B2 | 2/2003 | Ein-Gal |
| 6,600,810 | B1 * | 7/2003 | Hughes ........................ 378/152 |
| 7,095,823 | B2 | 8/2006 | Topolnjak et al. |

(Continued)

FOREIGN PATENT DOCUMENTS

| EP | 0562644 A1 | 9/1993 |
|---|---|---|
| JP | 03009767 | 1/1991 |
| JP | 07-067491 B2 | 7/1995 |

OTHER PUBLICATIONS

PCT, International Search Report and Written Opinion in International Application No. PCT/US2011/048201, Mar. 19, 2012, 12 pages.
State Intellectual Property Office of China, Office Action in Chinese Application No. 201180042837.7, Feb. 6, 2015, 11 pages.

*Primary Examiner* — Nicole Ippolito
(74) *Attorney, Agent, or Firm* — Houst Consulting

(57) ABSTRACT

A multilevel MLC includes a first set and a second set of a plurality of pairs of beam blocking leaves arranged adjacent one another. Leaves of each pair in the first set are disposed in an opposed relationship and longitudinally movable relative to each other in a first direction. Leaves of each pair in the second set are disposed in an opposed relationship and longitudinally movable relative to each other in a second direction generally parallel to the first direction. The first and second sets of pairs of leaves are disposed in different planes.

14 Claims, 8 Drawing Sheets

(56) References Cited

U.S. PATENT DOCUMENTS

| | | | |
|---|---|---|---|
| 8,637,841 B2 * | 1/2014 | Prince et al. | 250/505.1 |
| 2001/0043669 A1 | 11/2001 | Ein-Gal | |
| 2004/0184578 A1 | 9/2004 | Nakano | |
| 2005/0008123 A1 | 1/2005 | Topolnjak et al. | |
| 2006/0193441 A1 | 8/2006 | Cadman | |
| 2009/0207975 A1 | 8/2009 | Bourne | |
| 2010/0189220 A1 | 7/2010 | Flynn et al. | |

* cited by examiner

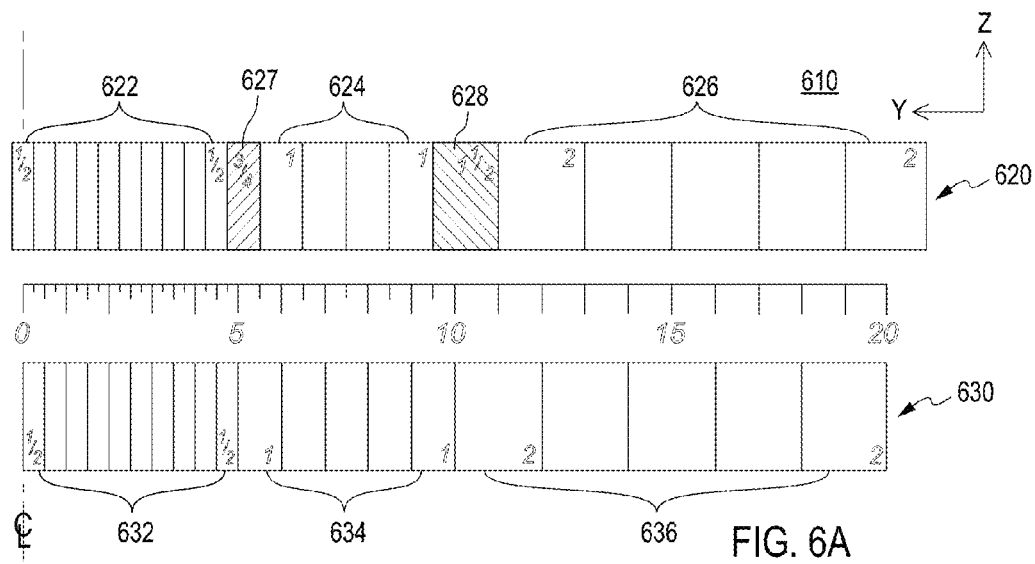
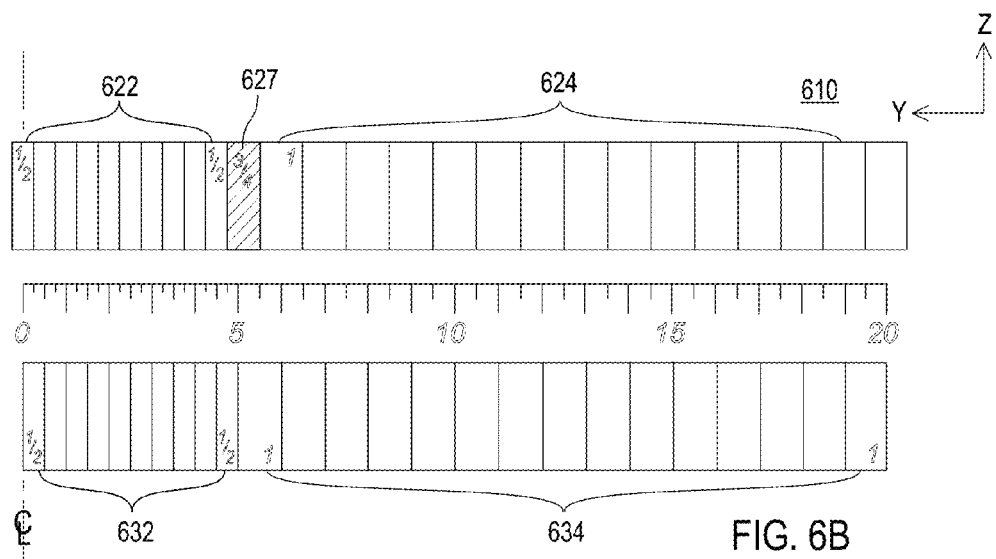
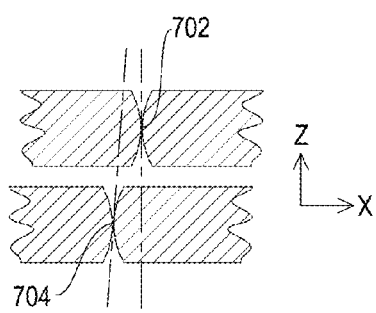
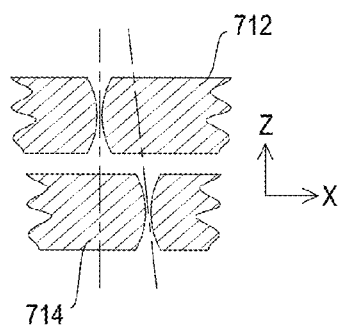
FIG. 6A
FIG. 6B
FIG. 7A
FIG. 7B

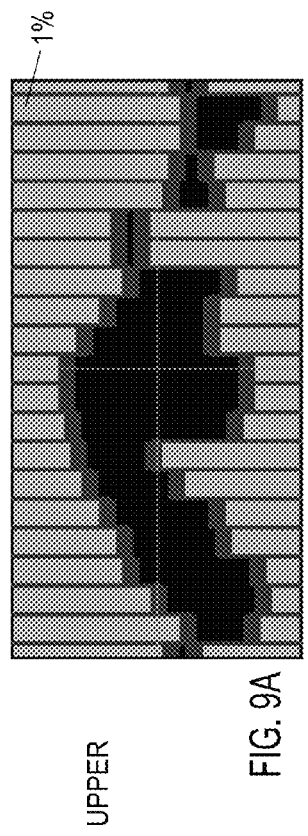
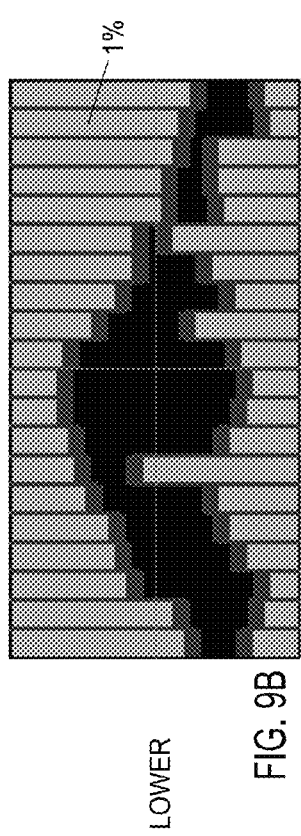
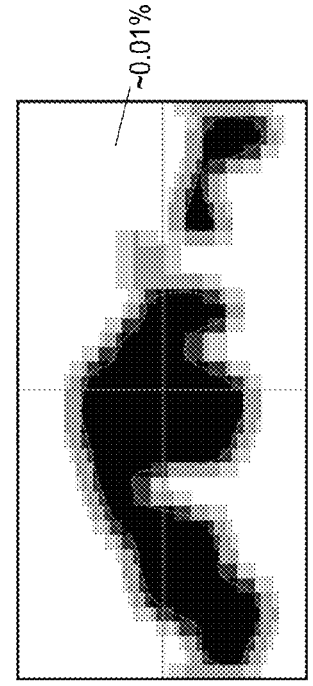
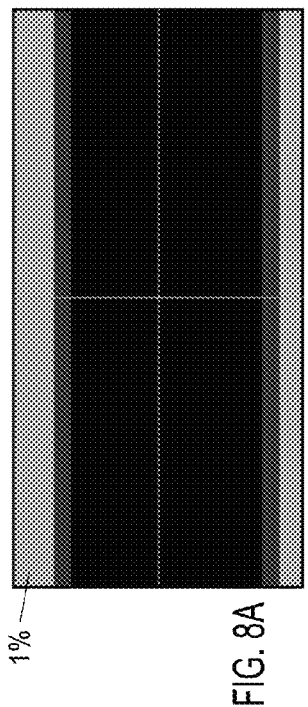
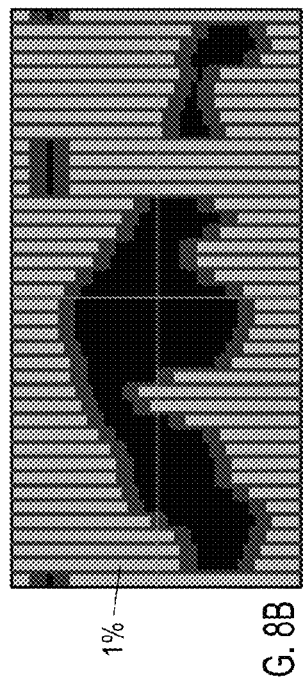
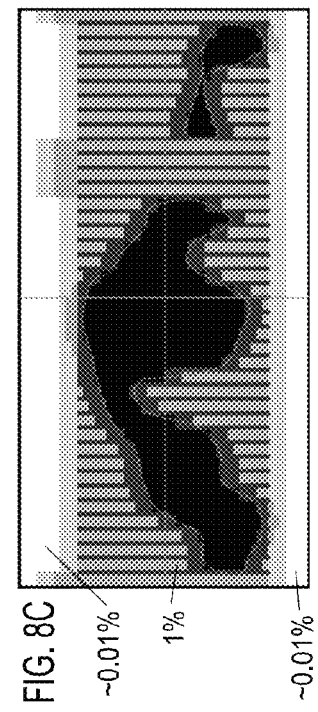
FIG. 8A  FIG. 8B  FIG. 8C
CONVENTIONAL MLC + JAWS
FIG. 9A  FIG. 9B  FIG. 9C
TWO LEVEL MLC
UPPER  LOWER  COMBO

MULTI LEVEL MULTILEAF COLLIMATORS

CROSS-REFERENCE TO RELATED APPLICATIONS

This application is a continuation of U.S. application Ser. No. 12/861,368 filed Aug. 23, 2010, entitled "Multi Level Multileaf Collimators," the disclosures of all of which are incorporated herein by reference.

BACKGROUND

This invention relates generally to radiation apparatuses and methods, and in particular to multileaf collimators and methods of adjusting radiation beams useful in radiotherapy and other industries.

Multileaf collimators (MLCs) are widely used in radiotherapy machines to support various treatments including intensity-modulated radiation therapy (IMRT) and arc therapy, etc. Conventional multileaf collimators include a single level of a plurality of beam blocking leaves arranged in two opposing banks or arrays. Each leaf in a bank is longitudinally movable relative to a leaf in the opposing bank. In operation each of the individual leaves is positioned to block a portion of a radiation beam passing through the volume occupied by the leaf. The combined positioning of all leaves defines one or many apertures through which the unblocked radiation beam passes, and the aperture(s) define(s) the shape of the radiation beam directed to a treatment field at an isocenter.

To mitigate radiation leakage in single level MLCs, various leaf designs are developed including "tongue in groove" designs in which steps, waves or similar geometries are provided on the leaf sides so that leaf materials mutually overlap between leaves as viewed from a radiation source. While a tongue in groove design may reduce leakage between leaf sides, it unfortunately leads to undesirable underdose effects when MLC treatment fields are combined. Some conventional MLCs are used in combination with one or two pairs of collimation jaws to reduce leakage between abutted leaf ends. One issue associated with the combination of a MLC with collimation jaws is the increased bulk of a radiation system and the resulting reduced clearance between the patient and moving equipment.

It is desirable to provide MLCs that can shape beams with high resolution so that the shaped beam conforms to a target volume as close as possible. In general a MLC would provide for higher beam shaping resolution if the beam blocking leaves could be thinner. However, reducing the width of leaves to improve MLC resolution has limitations and imposes challenges to MLC construction and operation. For MLCs using screw leaf drive systems for example, long slender drive screws may be susceptible to column buckling in a way that scales dramatically worse with smaller screw diameters. Motors with a smaller diameter may also be required.

SUMMARY

This invention provides for multi level MLCs and methods of shaping beams that can significantly reduce various leakage effects and improve beam shaping resolution. In some embodiments, a multilevel MLC comprises a first set and a second set of a plurality of pairs of beam blocking leaves arranged adjacent to one another. Leaves of each pair in the first set are disposed in an opposed relationship and longitudinally movable relative to each other in a first direction. Leaves of each pair in the second set are disposed in an opposed relationship and longitudinally movable relative to each other in a second direction generally parallel to the first direction. The first and second sets of pairs of leaves are disposed in different planes.

In some embodiments, each of the first and second sets includes a first section of a plurality of pairs of leaves having a first cross section and a second section of a plurality of pairs of leaves having a second cross section different from the first cross section. In some embodiments, the first cross section of the leaves in the first section of the first set is different from the first cross section of the leaves in the first section of the second set.

In some embodiments, the leaves in the first and second sets substantially focus on a single converging point. The leaves may have a trapezoidal cross section and generally flat side surfaces. Each leaf in the first set may be offset from a leaf in the second set in a direction generally traverse to the first and second directions. The leaves in the first and second sets may be supported by one or more movable carriages.

In some embodiments, each leaf in the first set is offset from a leaf in the second set by substantially half the leaf in a direction generally traverse to the first and second directions. The leaves in the first set may have a substantially same first cross section and the leaves in the second set may have a substantially same second cross section.

In one aspect a method of shaping radiation beams using a multi level MLC is provided. The multi level MLC comprises first and second sets of a plurality of beam blocking leaves disposed in first and second planes. Leaves in each of the first and second sets are arranged in two opposing arrays forming a plurality of pairs of leaves in the first and second sets respectively. Leaves of each pair are arranged in an opposed relationship and longitudinally movable relative each other, and the longitudinal moving directions are substantially parallel generally traverse to a beam direction. The leaves in the first and second sets are moved to block a selected portion of a radiation beam. In moving the leaves to produce treatment fields, generally, at least a portion of at least one leaf in an array of the first set overlaps at least a portion of at least one leaf in an opposing array of the second set in the beam direction. In some embodiments, the at least one leaf in the first set can come in contact with a leaf in an opposing array in the first set. In some embodiments, the at least one leaf in the first set can come in contact with a leaf in an opposing array in the first set at a first position, and the at least one leaf in the second set can come in contact with a leaf in an opposing array of the second set at a second position that is offset from the first position in the leaf moving directions.

BRIEF DESCRIPTION OF THE DRAWINGS

These and various other features and advantages will become better understood upon reading of the following detailed description in conjunction with the accompanying drawings and the appended claims provided below, where:

FIGS. 6A-6B are a cross-sectional view of a portion of an exemplary multi level MLC in accordance with some embodiments;

FIG. 7A schematically illustrates an exemplary MLC leaf control method in which abutted leaf ends at different levels close at positions offset in the leaf moving directions;

FIG. 7B schematically illustrates an exemplary MLC leaf control method in which abutted leaf ends at different levels do not physically touch each other;

FIGS. 8A-8C illustrate a prior art beam shaping method;

FIGS. 9A-9C illustrate an exemplary beam shaping method in accordance with some embodiments of the invention;

DETAILED DESCRIPTION

Figure 1:
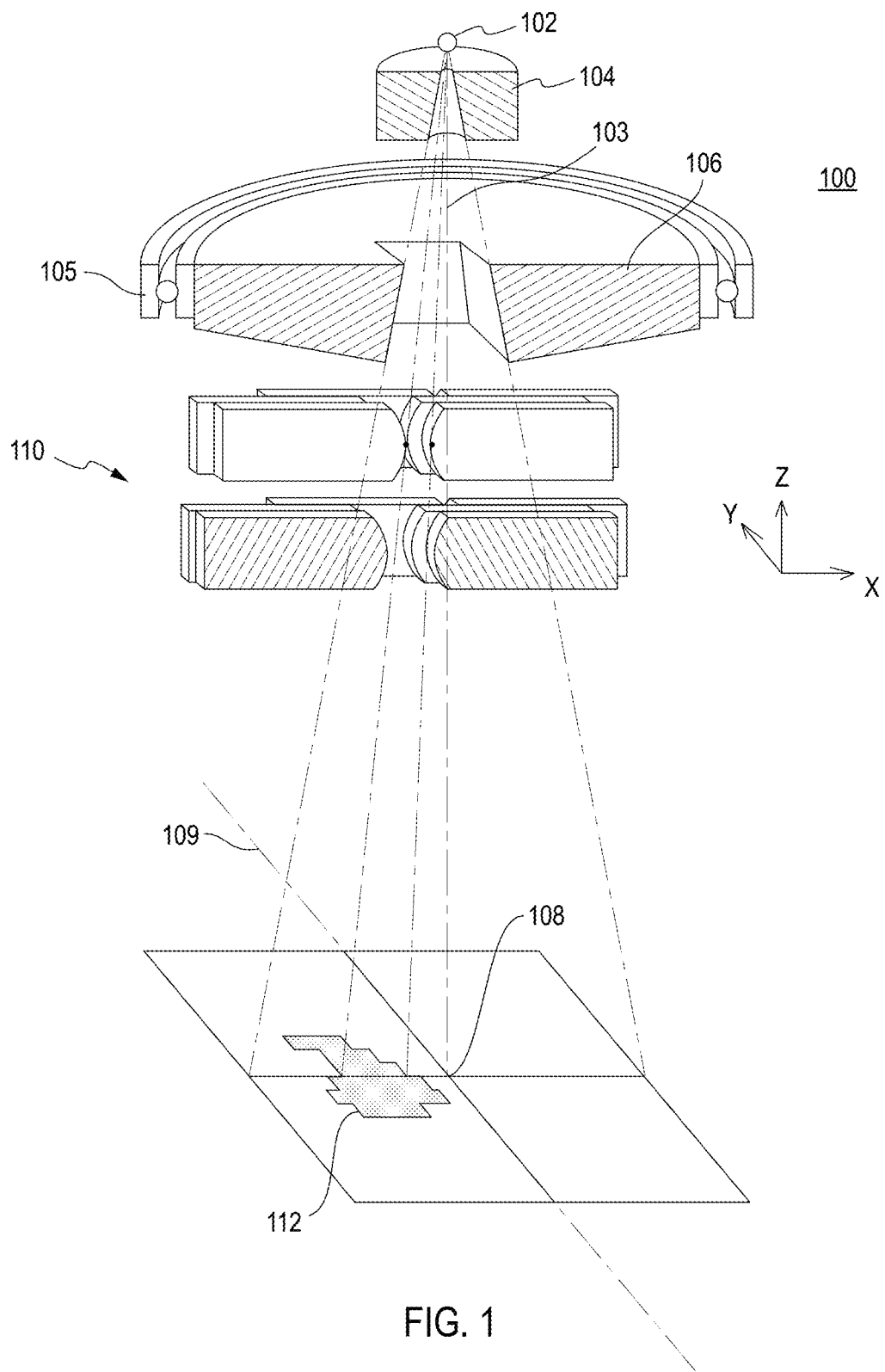
FIG. 1 is a schematic diagram illustrating a radiation system that includes a multi level MLC in accordance with some embodiments of the invention.

Various embodiments of multi level MLCs are described. It is to be understood that the invention is not limited to the particular embodiments described as such and may, of course, vary. An aspect described in conjunction with a particular embodiment is not necessarily limited to that embodiment and can be practiced in any other embodiments. For instance, while various embodiments are described in connection with X-ray radiotherapy machines, it will be appreciated that the invention can also be practiced in other electromagnetic apparatuses and modalities. It is also to be understood that the terminology used herein is for the purpose of describing particular embodiments only, and is not intended to be limiting since the scope of the invention will be defined by the appended claims, along with the full scope of equivalents to which such claims are entitled. In addition, various embodiments are described with reference to the figures. It should be noted that the figures are not drawn to scale, and are only intended to facilitate the description of specific embodiments. They are not intended as an exhaustive description or as a limitation on the scope of the invention.

Various relative terms such as "upper," "above," "top," "over," "on," "below," "under," "bottom," "higher," "lower" or similar terms may be used herein for convenience in describing relative positions, directions, or spatial relationships in conjunction with the drawings. For example, the term "level" or "upper or lower level" may be used for ease of describing some embodiments when a radiation source is on the top of an isocenter and a multi level MLC is positioned therebetween. The use of the relative terms should not be construed as to imply a necessary positioning, orientation, or direction of the structures or portions thereof in manufacturing or use, and to limit the scope of the invention. As used in the description and appended claims, the singular forms of "a," "an," and "the" include plural references unless the context clearly dictates otherwise. For example, reference to "a direction" includes the opposite direction of the direction and a plurality of directions that are parallel to the direction. A direction includes both linear and arc trajectories. As used herein the term "support body" may include a single support body member or a support body assembly comprised of a plurality of body members. The term "plane" as used in the plane of beam blocking leaves include both planar and curved or cylindrical planes.

In general, the present invention provides a multi level MLC that includes two or more sets of beam blocking leaves in two or more different levels or planes. The two or more sets of leaves may be arranged stacked one above the other and parallel so that all leaves may travel in a substantially same direction. The two or more sets of leaves may also be arranged offset such that each leaf in a set may be offset from a leaf in a different set in a direction generally traverse to the leaf travel direction.

FIG. 1 is a simplified illustration of a radiation system 100 that includes an exemplary multi level MLC in accordance with some embodiments of the invention. The radiation system 100 includes a radiation source 102 that is configured to produce beams 103 such as of photons, electrons, protons, or other types of radiation. For example, in X-ray radiotherapy the radiation source 102 may include a target which can produce X-ray radiation when impinged by energetic electron beams. The radiation system 100 may include beam shaping components such as a primary collimator 104 and optionally a secondary collimator 106 to generally limit the extent of the beam as it travels away from the radiation source 102 toward an isocenter 108. A multi level MLC 110 can be disposed between the radiation source 102 and the isocenter 108 to further adjust the shape and/or intensity of the beam 103 projected toward the isocenter 108. The MLC 110 and optionally a secondary collimator 106 may rotate about an axis through the source 102 and the isocenter 108, facilitated by bearing 105. The radiation source 102, primary collimator 104, bearing 105, secondary collimator 106, and MLC 110 may be enclosed in or attached to a structure such as a gantry, which may rotate about an axis such as a horizontal axis 109 through the isocenter 108. Thus in some embodiments, the radiation system 100 can deliver a treatment beam to a target in the isocenter plane 108 from various angles, and the shape and/or intensity of the beam can be dynamically adjusted by the MLC 110 as the beam angle is swept or stepped around the target.

The radiation system 100 may also include various other components which are not shown in FIG. 1 in order to simplify the description of the invention. For example, the radiation system 100 may include a flattening filter for providing uniform dose distribution, an ion chamber for monitoring the parameters of a beam, and a field light system for simulation of a treatment field, etc. The radiation system 100 may also optionally include one or two pairs of collimation jaws movable in x- and/or y-directions (lower jaws, upper jaws) to provide for rectangular shaping of beams. In some embodiments, the radiation system 100 may include one of the collimation jaw pairs in conjunction with a multi level MLC of the invention. In some embodiments, the radiation system 100 does not require collimation jaws; the inclusion of a multi level MLC of the invention may effectively replace both the upper and lower jaws. As will be described in greater detail below, the design and control of the multi level MLC of the invention can significantly reduce various leakage effects, thus additional collimation jaws would not be required. Replacement of conventional collimation jaws would be an advantage as it reduces the bulk of a radiation system and improves the clearance between the patient and moving equipment.

Figure 2:
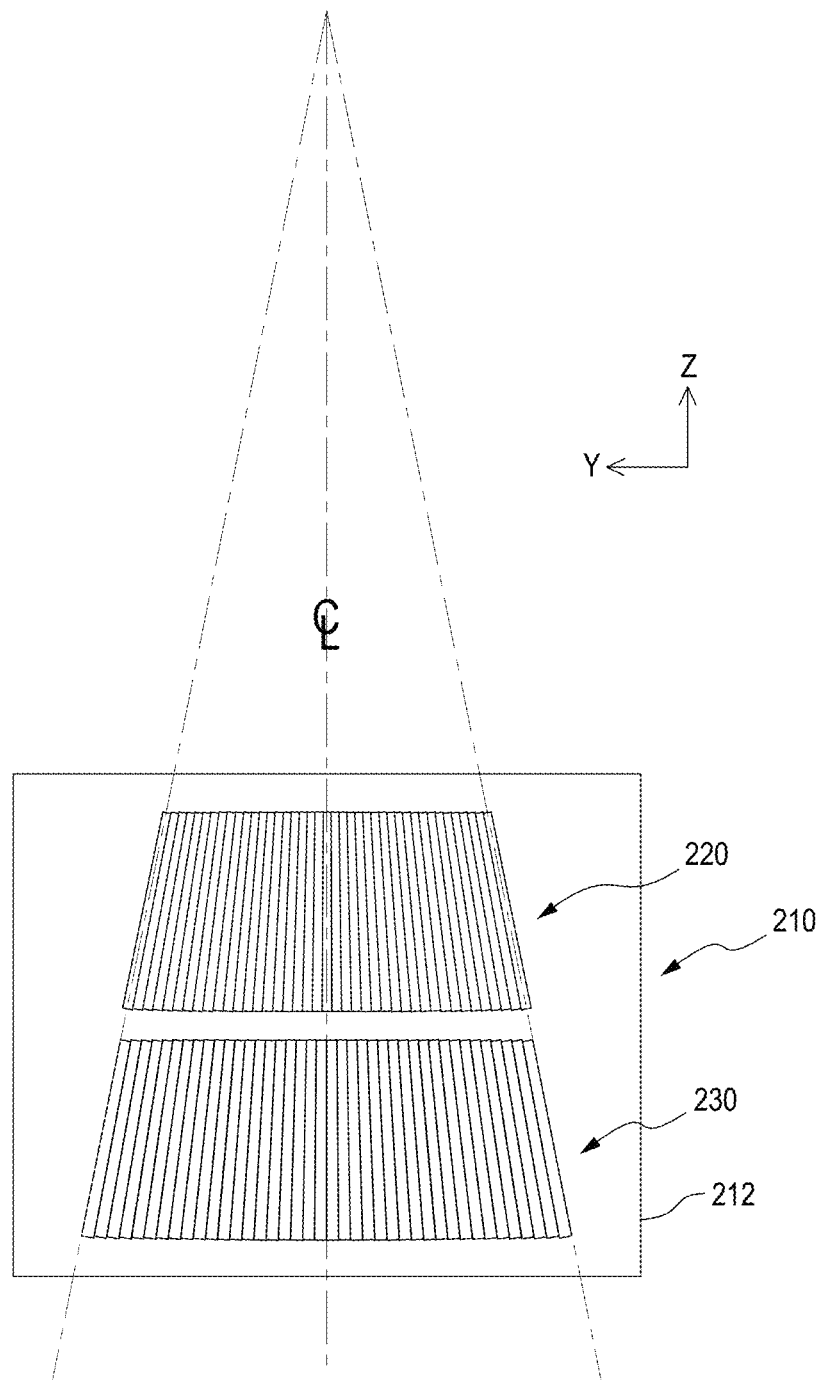
FIG. 2 is a cross-sectional view of an exemplary multi level MLC in accordance with some embodiments of the invention.

FIG. 2 is a cross-sectional view of an exemplary multi level MLC 210 in accordance with some embodiments. To simplify description, two sets of beam blocking leaves at two different levels or planes are shown in FIG. 2. It will be appreciated that three or more sets of leaves can be arranged at three or more different levels. As shown, the two or more sets 220, 230 can be arranged stacked and parallel. In each set, a plurality of leaves may be arranged in two banks or arrays forming a plurality of pairs of opposing leaves. Each leaf of a pair in a bank can be longitudinally movable relative to the other leaf of the pair in the opposing bank. In some embodiments, the two or more sets 220, 230 can be arranged such that the leaves at different levels may travel in a same direction. For example, the two or more sets 220, 230 may be arranged such that all the leaves in the MLC 210 can travel in e.g. the x-direction generally traverse to the beam direction when in use.

Figure 3:
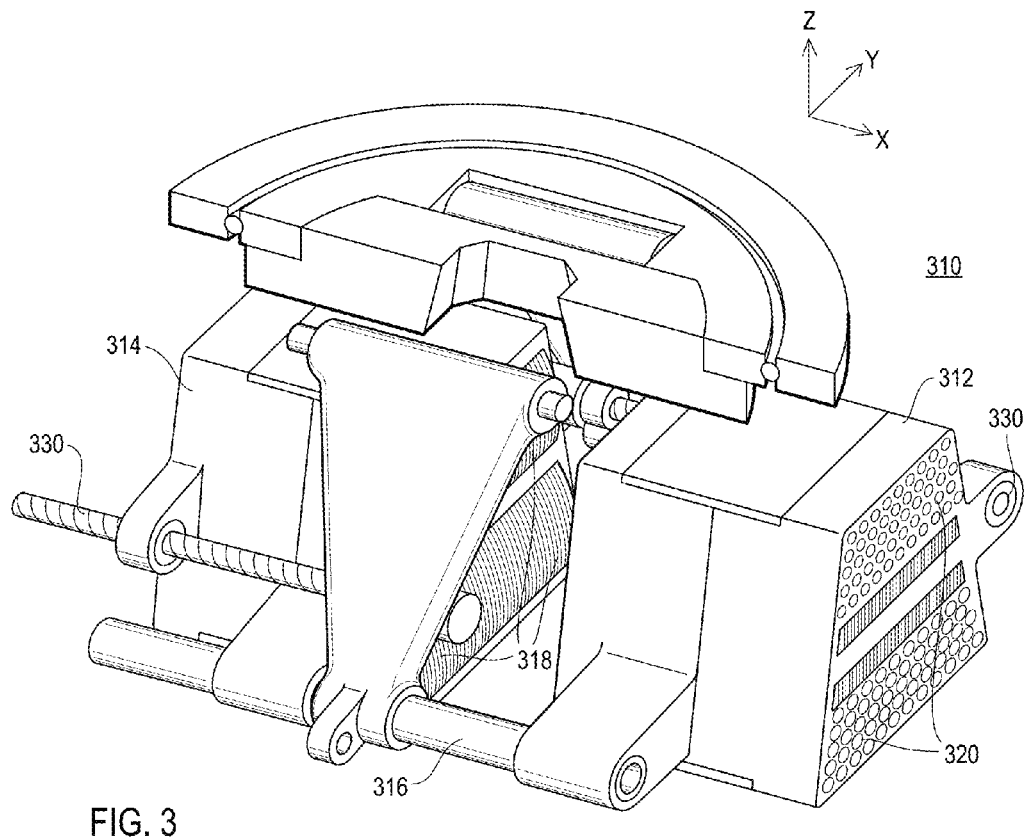
FIG. 3 is an isometric view of an exemplary multi level MLC in accordance with some embodiments of the invention.

The leaves of the MLC can be supported by a support body 212 which may include such as frames, boxes, carriages or other support structures. In some embodiments all the MLC leaves in different sets 220, 230 can be supported by a single carriage (unicarriage). The single carriage, supporting all the MLC leaves, can be driven such as by a powered actuating mechanism in the MLC leaf travel direction. In some embodiments, the MLC 210 may include two carriages each supports a portion of the MLC leaves or each supports a level of leaves. FIG. 3 illustrates an exemplary two level MLC 310 including two carriages 312, 314. One carriage 312 may support half the MLC leaves on a same side of all levels, and the other carriage 314 supports the other half on the opposing side. The two carriages 312, 314, each supporting half the MLC leaves, can be independently moved by powered actuating mechanism 330 along the MLC leaf travel direction. The carriages 312, 314 may travel on guide rails 316. Numerous arrangements and types of guide rails and powered actuators could be used to support and move carriages. The use of one or more carriages may provide advantages in that individual leaves and their travel can be shorter, and therefore have better tolerance control, less cost, less weight, and can fit in a smaller cover or similar structures. Combined speed of leaves and carriages can be a treatment planning advantage. In some embodiments, the multi level MLC of the invention does not require a movable carriage or carriages (carriageless).

As shown in FIG. 3, each of the MLC leaves 318 can be independently moved by an associated drive motor 320. The drive motors 320 can be secured to the support body such as a carriage or carriages 312, 314 and are coupled to position feedback devices, a computer and motion control (not shown). In operation the drive motors 320 receive signals from the computer and motion control and move to position individual leaves 318 relative to the beam direction based on a treatment plan. The positioning of a leaf operates to block or adjust the radiation beam which is passing through the volume occupied by the leaf. The combined positioning of all leaves may define one or more aperture(s) through which an unblocked radiation beam passes, and the aperture(s) may define the shape of the radiation beam projected to a target which may be located in the isocenter plane.

Returning to FIG. 1, the shape of the radiation beam 103 projected on the isocenter plane 108 has a step or strip resolution at the beam boundary 112. The step resolution is a function of the width of individual leaves of the MLC 110 and the position of the leaves relative to the isocenter 108 and the radiation source 102 from which the beam is emitted and diverged. In general, the step resolution would be higher if the leaves of the MLC 110 were thinner. Higher step resolution can also be provided by positioning the MLC 110 closer to the isocenter 108. In the description of the MLC definition and various radiation leakage effects, the terms of "length," "width," "height," "side," and "end" of a leaf may be used. The "length" of a leaf as used herein refers to the leaf dimension that is parallel to the leaf moving direction. The "width" of a leaf refers to the dimension of the leaf that is traverse the leaf moving direction and the direction of the radiation beam. The "height" of a leaf refers to the dimension of the leaf along the beam direction. The "side" of a leaf refers to the surface adjacent to neighboring leaves in a bank. The "end" of a leaf refers to the surface of the leaf inserted into the field along the length.

Figure 4:
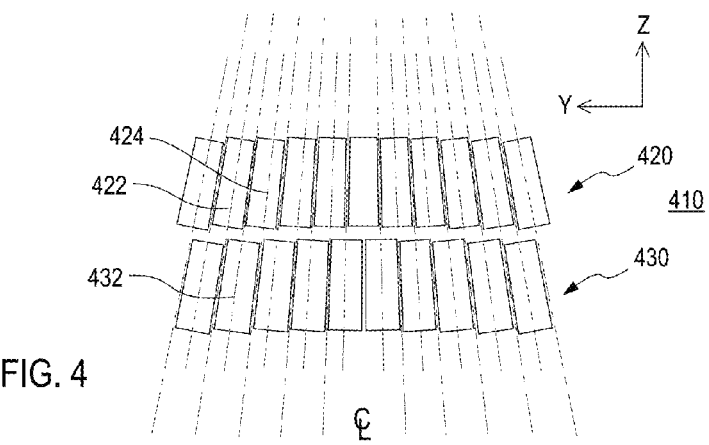
FIG. 4 is a cross-sectional view of a portion of an exemplary multi level MLC in accordance with some embodiments of the invention.

FIG. 4 is a cross-sectional view of a portion of a multi level MLC 410 showing some detail of the leaf arrangement in accordance with some embodiments. As shown, first and second sets of leaves 420, 430 may be arranged at two different levels. In some embodiments, the first and second sets 420, 430 can be disposed such that each leaf in a set (e.g. leaf 422 in the first set 420) can be offset from a leaf in another set (e.g. leaf 432 in the second set 430) along a lateral direction or a direction traverse to the leaf moving direction. For example in some embodiments, a leaf in the first set 420 or second set 430 can be offset from a leaf in the second set 430 or first set 420 by substantially half a leaf. Alternatively, in some embodiments the first and second sets 420, 430 are disposed such that the gap between two adjacent leaves at a level (e.g. the gap between leaves 422, 424 in the first set 420) is positioned substantially at the middle of a leaf in another set (e.g. leaf 432 in the second set 430). The offset arrangement of leaves at different levels provides for leaf projections that are also offset at the isocenter. Therefore, in some embodiments the leaves in the first and second sets 420, 430 are arranged offset each other to provide for projections offset by approximately half a leaf width as projected at the isocenter plane. This provides for substantially an equivalent of doubling MLC definition, or improving the step resolution to half as compared to the definition of a single level MLC with leaves of the same physical width. In some embodiments, the MLC may include three or more sets of leaves at three or more levels which may be arranged such that each leaf at a level is offset e.g. by ⅓ or 1/n of leaf width as projected at the isocenter where n is the number of sets of the MLC. In embodiments with offset leaf arrangement, the number of leaves at a level may be different from the number of leaves at another level. For example, in a two level MLC, a leaf array at the upper level may include one more leaf than a leaf array at the lower level to ensure coverage by at least one single leaf at the sides of a symmetric MLC field.

The leaves in a set at a level may have a substantially same cross-section. For example, in some embodiments the leaves in a set may have a same trapezoidal cross-section. Other cross-sectional shapes of leaves such as rectangular shape, tilted trapezoids, or trapezoids with stepped or wavy sides are possible. Alternating patterns of cross-sections are also possible, such as trapezoid, rectangle, trapezoid, rectangle, and so on. The cross-sectional shapes described herein do not refer to additional detail features in the cross-section that provide support and guidance for the leaves, such as added hook or tab shapes. Due to divergence of radiation beam from a source, the physical width of leaves at different levels may be different to provide the same projected width definition at the isocenter. For example, the leaves in a set closer to a source may have a narrower cross section than that of the leaves in a set farther from the source. In some embodiments, the leaves in the first and second sets may be arranged tilted or inclined to the source or substantially focus on a converging virtual point located substantially at the source. The focused leaf arrangement may improve the quality of beam shaping at the isocenter.

The leaf side surfaces may be flat. In some embodiments, the adjacent leaf side surfaces may form a gap or spacing ranging from approximately 10 to 100 micrometers to facilitate relative movement between the leaves. The leaf side gaps may be substantially the same at a level. Because leaves at a level may cover radiation leakage between leaf sides (gap leakage) at another level, the leaf sides of the multi level MLC of the invention require little or no "tongue in groove" design as in conventional MLCs. In some embodiments, the leaves may have a trapezoidal cross section and the leaves may be arranged such that the leaf side surfaces substantially focus on a converging virtual point located substantially at the radiation source. This arrangement may provide the least leaf side penumbra. This arrangement can also eliminate or minimize "tongue and groove effect" because at a leaf level there is substantially no leaf material overlap between leaves as viewed from the radiation source. In a real situation where the radiation source is of finite size, rather than a theoretical point, the radiation may be thought to emanate from various "pixels" within that finite source and, the leaf side surfaces may not be viewed as perfectly focused from every source pixel, and leaf overlap material at a leaf level may contribute a slight tongue and groove effect from some of those pixels. Rather than an ideal focus on the source, a practical compromise such as a small step, wave, or a very slight defocused tilt may prove to be a better balance between gap leakage and tongue and groove effects.

Figure 5:
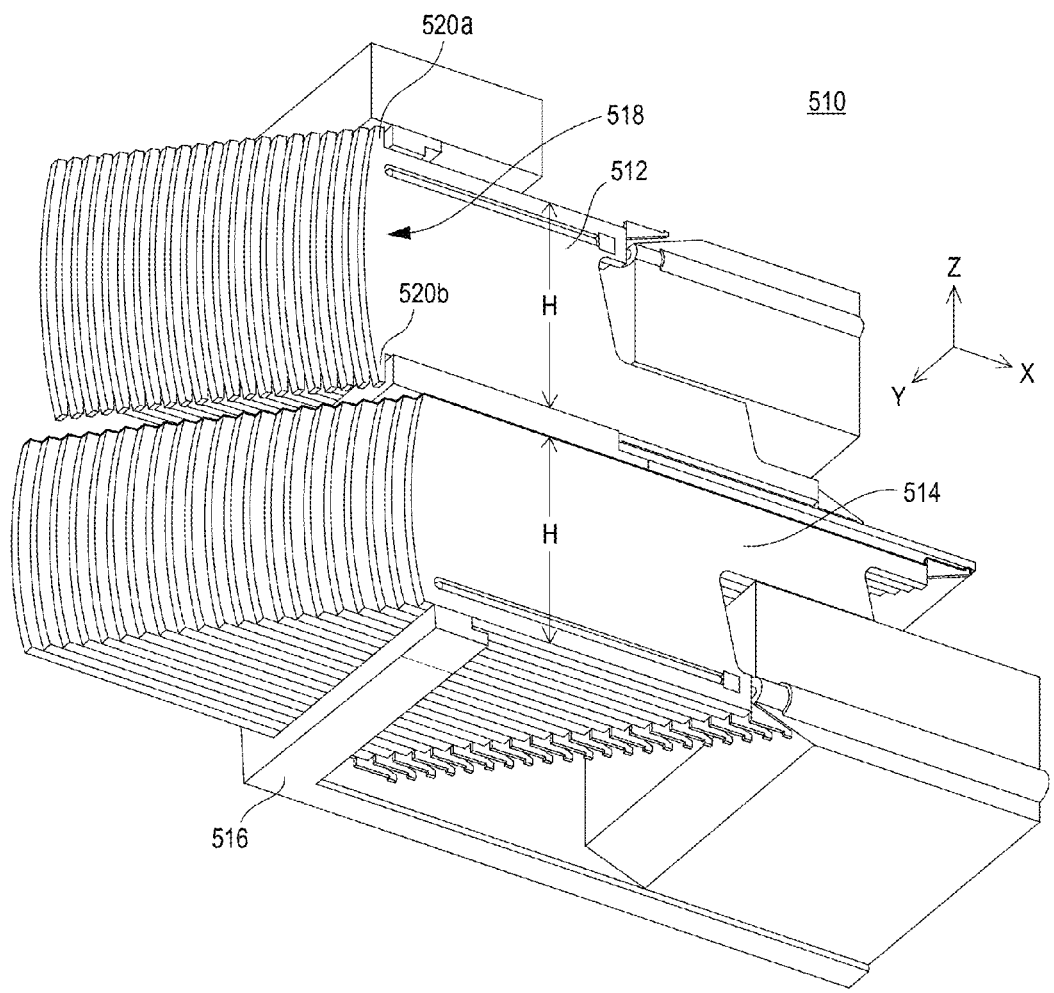
FIG. 5 is an isometric cut-away view of an exemplary multi level MLC in accordance with some embodiments of the invention.

The leaf ends can be round, flat, or in various other configurations. The penumbra of leaf ends closer to the source will tend to be greater than the penumbra of leaf ends farther from the source due to geometric projection effects of the radiation source. For treatment planning purposes, it would be desirable if leaf ends have approximately same penumbra. For leaf ends that are substantially rounded, the otherwise worse penumbra of the upper leaves can be partially mitigated by using a larger leaf end radius. A larger radius reduces the penumbra due to transmission through the leaf material (e.g. tungsten). A larger leaf end radius may require taller leaves. Therefore, in some embodiment the height of the upper level leaves is greater than the height of the lower level leaves to insure approximately constant penumbra over the entire leaf travel range. In some embodiments the height of the upper level leaves and the lower level leaves is substantially the same, but the upper level leaves have an end portion with a larger radius. FIG. 5 shows with greater detail the end portion of the upper level leaves in an exemplary MLC 510. The MLC 510 includes upper level leaves 512 and lower level leaves 514 supported by a support body such as a leaf box 516. The upper leaves 512 and lower level leaves 514 may have a main portion of substantially same height ("H" as shown). The end portion 518 of the upper level leaves 512 may have one or two "tooth" portions or projections 520a, 520b extended e.g. either upward or downward, or extended both upward and downward to allow an increase of the leaf end radius of the upper leaves 512. The extended radius can mitigate the penumbra of the upper leaves 512 without substantially increasing the weight or height of the upper level leaf bodies. Not increasing the leaf body weight beyond what is needed for shielding is desirable due to packaging volume and leaf weight constraints. The tooth extensions 520a, 520b may be located outside of the leaf box 516 and use the space not otherwise needed. The resulting upper leaves 512 may have an end portion 518 with a "mushroom" shape in side view. If necessary to further mitigate unequal leaf end penumbra between the upper and lower levels, the radius of the lower leaf ends can be reduced below the maximum radius allowed by the leaf height.

The leaves may be constructed with various suitable radiation attenuating materials. To generally improve on leakage performance of existing beam limiting devices, the combined attenuation of all levels of the MLC should be approximately 2.5 tenth value layers ("TVLs") or greater. Single leaves at one level should substantially mitigate the local leakage of leaf gaps at another level. In general, the leaf gap leakage that can be allowed at a level in the multi level MLC can be greater as compared to conventional single level MLCs since the leaves at another level can mitigate the gap leakage. Since small areas at the prescribed boundaries of treatment fields may be covered by only a single leaf, the leaf height should be 1.5 TVLs or greater to perform adequately.

In some embodiments, the multi level MLC of the invention can provide for a treatment field that is shaped by leaves all having the same width definition at the isocenter. By way of example, a treatment field of 40×40 cm$^2$ with a projected leaf width of ½ cm (¼ cm offset definition) can be provided using 322 individual leaves disposed at two levels. As another example, a treatment field of 40×40 cm$^2$ with a projected leaf width of 1 cm (½ cm offset definition) can be provided using 162 individual leaves. It will be appreciated that treatment fields of different sizes with different width definitions can be provided by the multi level MLCs of the invention including different numbers of individual leaves based on specific applications.

In some embodiments, the multi level MLC of the invention may provide for a treatment field that is shaped by leaves of different width definitions at the isocenter. The finer definition (e.g. ¼ cm) may be provided in the central portion of the treatment field where precision is more needed. This may reduce MLC cost and increase MLC reliability compared to an MLC with a greater number of leaves allowing fine definition throughout the entire treatment field. In an embodiment, the transition of leaf width can be gradual. For example, the width of leaves at a level can be progressively increased with distance from the center of the treatment field. Each leaf at a level may have a physically different width dimension. Alternatively, each MLC level may include leaf sections so that the transition of leaf widths is discreet. The transition can be made by placing transition leaves at specific locations on one or both levels. The transition leaves insure that the gaps between leaves project at the desired spacing for the desired definition regions.

FIG. 6A is a cross-sectional view of a portion of an exemplary multi level MLC 610 providing variable width definition in accordance with some embodiments. The MLC 610 may include two or more sets of leaves 620, 630 of different sizes which project different leaf widths at the isocenter (e.g., ½, 1, 2 cm etc.). To simplify description, leaves at a level are shown as having a rectangular cross-section to better illustrate the offset arrangement of leaves at different levels. Leaves may have a cross-section of trapezoidal, rectangular, or other shapes.

At a first level 620, the MLC 610 may include a first section of leaves 622 with a first cross-section that provides for a first substantially same width definition (e.g. ½ cm), a second section of leaves 624 with a second cross-section that provides for a second substantially same width definition (e.g. 1 cm), and optionally a third section of leaves 626 with a third cross-section that provides for a third substantially same width definition (e.g. 2 cm) at the isocenter, and so on. At a second level 630, the MLC 610 may include first, second, and optionally third sections of leaves 632, 634, 636 which may be arranged offset from the corresponding first, second, and optionally third sections of leaves 622, 624, 626 at the first level 620. The leaves of the first, second, and optionally third sections 632, 634, 636 at the second level 630 may have cross-sections that provide for width definitions at the isocenter substantially same as the first, second, and optionally third width definitions of the first level leaves 620 respectively. At one or both level(s) such as the first level 620, one or more transition leaves 627 may be disposed between the first and second sections 622, 624, or optionally one or more transition leaves 628 between the second and third sections 624, 626.

By way of example, the first sections of leaves 622, 632 at the first and second levels 620, 630 may provide for ½ cm width definition or ¼ cm offset definition at the isocenter, the second sections of leaves 624, 634 at the first and second levels 620, 630 may provide for 1 cm width definition or ½ cm offset definition, and optionally the third sections of leaves 626, 636 at the first and second levels 620, 630 may provide for 2 cm width definition or 1 cm offset definition. In some embodiments, a transition leaf 627 may provide for ¾ cm width definition, or optionally a transition leaf 628 may provide for 1 ½ cm width definition. It should be noted that the above leaf width dimensions are provided by way of example, and it will be appreciated that different width definitions may be provided for by a multi level MLC 610 including leaves of different sizes. A multi level MLC with variable width definitions allows the use of different types or sizes of leaves in the MLC. For example, the MLC may include high definition leaves in the middle section to define a treatment field closely conformal to the target. In the outer section where high definition may not be required, relatively low definition leaves may be used to reduce manufacturing cost and increase reliability of the MLC. By way of example, a multi level MLC with a variable leaf width configuration illustrated in FIG. 6A may provide a 40×40 cm² treatment field using only 162 leaves, which are far fewer than 322 leaves that would be required for ¼ cm definition across the full field. FIG. 6B illustrates another alternative embodiment with variable leaf widths which can provide a 40×40 cm² treatment field also with 10 cm of ¼ cm definition using 202 leaves.

In some aspect the invention provides for a method of shaping radiation beams. Using a multi level MLC and a control method provided by the invention, various radiation leakage can be significantly reduced. The leakage between leaf sides or gap leakage can be mitigated by using a multi level MLC with offset leaf arrangement (see FIGS. 3 and 6A-6B). As described above, a multi level MLC may include two or more sets of leaves at different levels, and leaves at each level may be arranged in two banks or arrays forming a plurality of pairs of opposing leaves at each level. The two or more sets of leaves may be disposed generally in parallel so that all the leaves of the multi level MLC may travel in a substantially same direction generally traverse to the beam direction. In a preferred embodiment, the two or more sets of leaves can be disposed such that leaves at a level are offset from leaves at another level in a lateral direction (e.g., y-direction) generally traverse to the leaf moving direction so that the leakage between leaf sides at a level can be mitigated by leaves at another level.

To reduce leakage between abutted leaf ends that may be intended to close in shaping a treatment field, the ends of the abutted leaves at a level may close at a position slightly offset, in the leaf travel direction (e.g., x-direction), from the position where the ends of the abutted leaves close at a different level. This would ensure that the abutted leaf end leakages are not superimposed but instead attenuated by at least a single leaf height. FIG. 7A schematically shows an exemplary embodiment where abutted leaf ends close at positions 702, 704, which are offset in the leaf travel direction (e.g. the x-direction) so that the rays through pairs of abutted ends are never superimposed. In execution, factors such as 3-dimensional effects including the presence of separated treatment field regions the relative x and y positions of their field boundaries, and whether an even or odd number of field strips separate regions etc. should be accounted for in determining the offset positions. In general as shown in FIG. 7B, the abutted leaf end leakage can be mitigated if a portion of a leaf 712 in a leaf bank at a level overlaps a portion of a leaf 714 in an opposing leaf bank at a different level as viewed from a radiation source. This would allow mitigation of abutted leaf end leakage to acceptable levels without ever having to touch the opposing abutted leaves together. For example, a minimum physical gap of less than 1 mm between abutted leaf ends should sufficiently control leakage, yet still be manageable within control accuracies. Not requiring abutted leaf ends to ever actually touch can reduce control program and leaf drive mechanical complexity and increase leaf drive reliability. Components such as springs and sacrificial "fuses" in a leaf drive nut as used in conventional MLCs to limit collision damage can also be eliminated if abutted leaf contact is not needed and such collisions become a rare event. Penumbra compromises associated with complex interlocking leaf end shapes can also be avoided. The ability to dynamically close leaf ends quickly, with low leakage, even between momentarily separated field regions can be an advantage to treatment planning. Such a creative offset control can be applied to dynamically changing field regions. Dynamically separating and recombining field regions can be created generally without even momentarily producing an unwanted region of high abutted leaf end leakage.

A multi level MLC and a method of shaping radiation beams have been described. One of the advantages of the multi level MLC is that the offset arrangement of leaves can effectively improve beam shaping resolution, and allow the same definition with leaves physically twice as wide as for a single level MLC. The extra physical leaf width is a considerable construction advantage for achieving equal or higher MLC definition in a more limited volume, particularly for screw leaf drive systems. For example, in screw leaf drive systems, long slender leaf drive screws may be susceptible to column buckling in a way that scales dramatically worse with smaller screw diameters. Since the leaf drive screw diameter is generally limited to not be greater than physical leaf width, the invention greatly reduces the screw drive susceptibility to column buckling by allowing leaf drive screws to be nearly doubled in diameter. In addition, wider leaves allow room for larger diameter motors. The general relaxation of leaf drive miniaturization can also allow more motor choices, faster leaf speeds, better manufacturing process control, higher performance margins, higher reliability, and easier service access. These advantages are all desirable for dynamic treatments and MLC cost is also reduced.

Another advantage of the invention is that the use of the multi level MLC can significantly improve the leakage effect over a single level MLC used in conjunction with one or two pairs of collimation jaws. FIGS. 8A-8C and FIGS. 9A-9C compare a conventional beam shaping method with some embodiments of the invention and their leakage effect. The gray tones of the figure approximate the transmission of the radiation beam passing through the MLC similar to how it would appear on film, with more radiation intensity being darker. To simplify calculations in this example, each level provides 2 Tenth Value Layer (TVL) attenuation. Thus the transmission of radiation through a single leaf for this example is assumed to be 1% of the intensity of the original unattenuated radiation beam. FIG. 8C shows intended radiation field regions shaped by corresponding positions of a pair of collimation jaws (FIG. 8A) and a single level MLC (FIG. 8B) acting in combination. FIG. 9C shows intended radiation field regions shaped by a multi level MLC of the invention including a first set (FIG. 9A) and a second set (FIG. 9B). In the conventional method, the combined leakage between the abutted leaf ends separating field regions and the leakage between leaf sides are evident as shown in FIG. 8C, whereas in the method using a multi level MLC of the invention, the combined leakage is significantly reduced as shown in FIG. 9C. Further, the combined leakage reduction of a conventional MLC shown in FIG. 8C is limited to a rectangle, while the combined leakage reduction of the multi level MLC of the invention extends nearly to the boundaries of the treatment field shown in FIG. 9C.

Figure 10A:
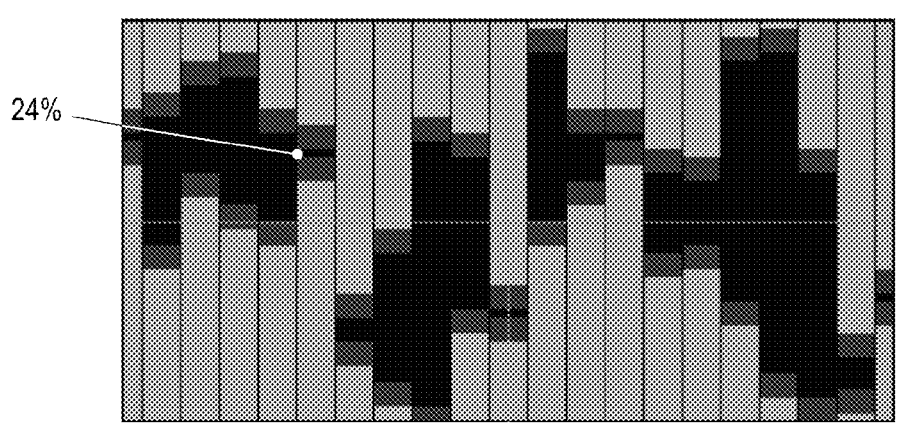
FIGS. 10A-10C illustrate an exemplary beam shaping method in accordance with some other embodiments of the invention.
Figure 10B:
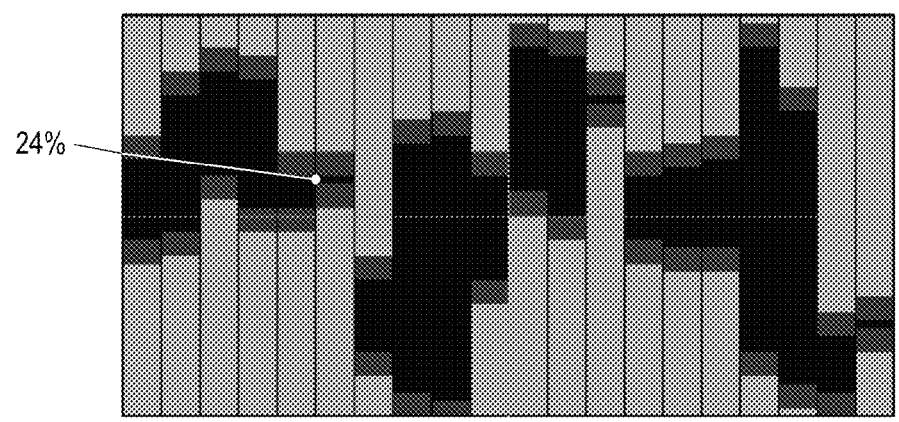
Figure 10C:
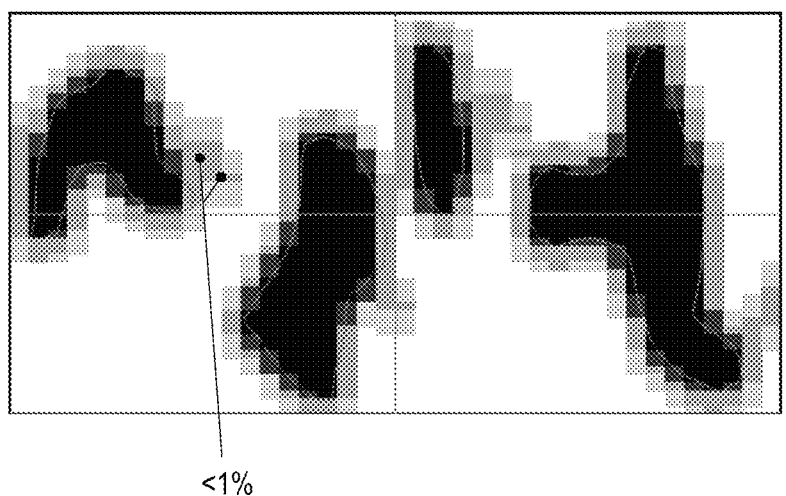

The leakage between abutted leaf ends can also be significantly mitigated using the control method described above. FIGS. 10A-10C show that the abutted leaf leakage between rounded leaf ends at a single level can be as much as 24% on the centerline. With the offset control in the leaf travel-direction between levels, the abutted leaf end leakage can be reduced to less than 1%, as shown in FIG. 10C. Treatment field regions can be quickly separated and recombined without high leakage.

Because the multi level MLC and control method provided by the invention can effectively reduce leaf leakage to acceptable levels, collimation jaws such as y-direction jaws are not required to control leaf end to end leakage as it is in most conventional single level MLCs. A fairly small and light-weight y-direction jaw pair may optionally be used in conjunction with the multi level MLC to provide for continuous adjustability of field width. A y-direction jaw pair might also mitigate small points of leakage where the abutted leaf gap of one level aligns with a leaf side gap of the other level.

Figure 11:
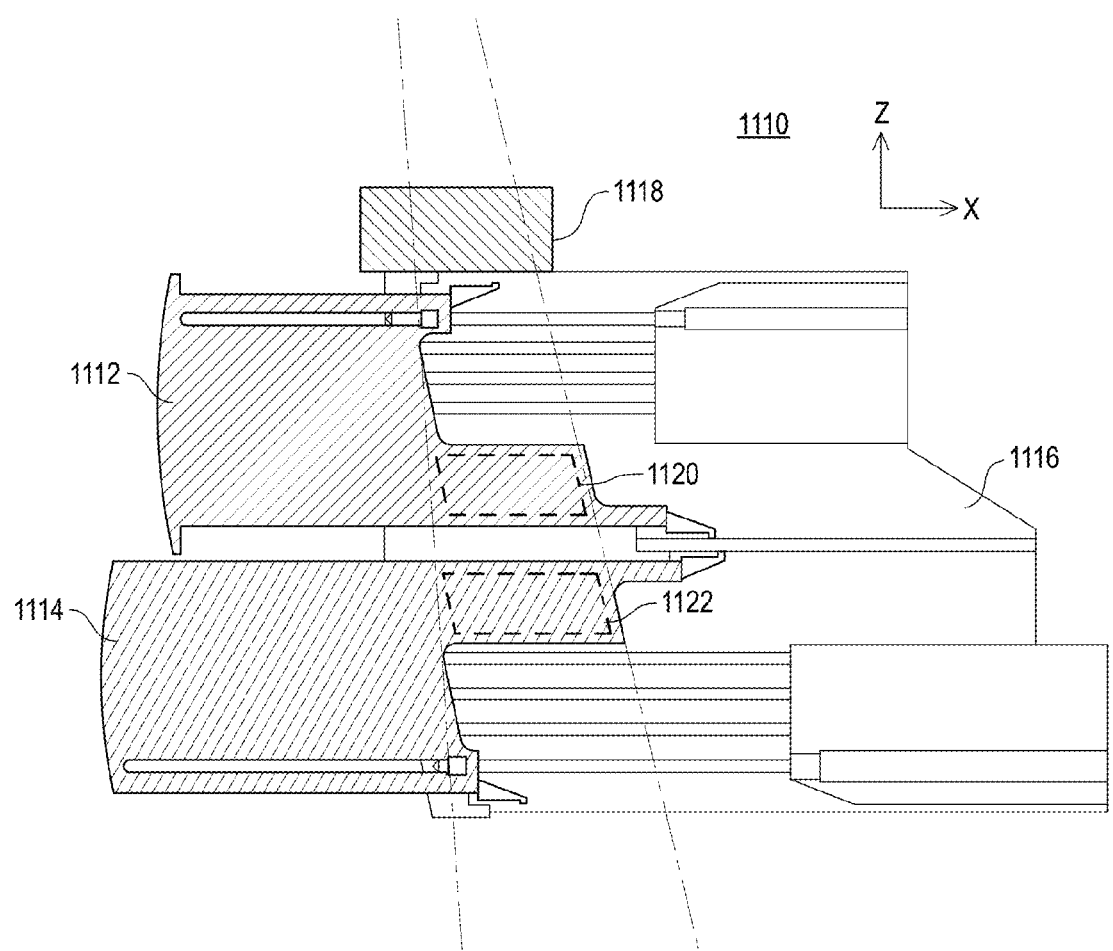
FIG. 11 is a side cross-sectional view of an exemplary multi level MLC in accordance with some embodiment.

Shielding fixed to carriages or to a unicarriage may be used to provide adequate TVL coverage under all use cases. FIG. 11 shows a side cross-sectional view of an exemplary two level MLC 1110 including upper level leaves 1112 and lower level leaves 1114 supported by a carriage 1116. A small shielding block 1118 can be fixed to the top of the carriage 1116 to insure adequate shielding under all use cases in combination with lowered leaf tail portions 1120, 1122.

The multi level MLC of the invention can be used in a radiotherapy machine to support various treatment options including intensity-modulated radiation therapy (IMRT), arc therapy, and other forms of radiotherapy. In intensity-modulated radiation therapy, the multi level MLC can be controlled to modulate the intensity and adjust the shape of the beam conformal to the size, shape, and location of the target. In dynamic arc therapy, the radiation source may rotate in delivery of radiation from various angles. The multi level MLC can be dynamically controlled during rotation of the source to adjust the beam conformal to the size, shape, and location of the target from various angles.

Those skilled in the art will appreciate that various other modifications may be made within the spirit and scope of the invention. All these or other variations and modifications are contemplated by the inventors and within the scope of the invention.

What is claimed is:

1. A multileaf collimator comprising:
    a first set of a plurality of pairs of beam blocking leaves arranged adjacent one another, leaves of each pair in the first set being disposed in an opposed relationship and longitudinally movable relative to each other in a first direction; and
    a second set of a plurality of pairs of beam blocking leaves arranged adjacent one another, leaves of each pair in the second set being disposed in an opposed relationship and longitudinally movable relative to each other in a second direction generally parallel to the first direction; wherein
    the first and second sets of pairs of leaves are disposed in different planes and the first set of pairs of leaves comprises a first quantity of pairs of leaves and the second set of pairs of leaves comprises a second quantity of pairs of leaves wherein the first quantity and the second quantity are different.

2. The multileaf collimator of claim 1 wherein the first quantity is greater than the second quantity by one pair.

3. The multileaf collimator of claim 1 wherein each leaf in the first set is offset from a leaf in the second set by about half a leaf width in a direction generally traverse to the first and second directions.

4. The multileaf collimator of claim 1 wherein the leaves in the first and second sets are supported by one or more movable carriages.

5. The multileaf collimator of claim 1 wherein the leaves in the first and second sets substantially focus on a converging virtual point located substantially at a radiation source.

6. A multileaf collimator comprising:
    a first set of a plurality of pairs of beam blocking leaves arranged adjacent one another, leaves of each pair in the first set being disposed in an opposed relationship and longitudinally movable relative to each other in a first direction; and
    a second set of a plurality of pairs of beam blocking leaves arranged adjacent one another, leaves of each pair in the second set being disposed in an opposed relationship and longitudinally movable relative to each other in a second direction generally parallel to the first direction; wherein
    the leaves of the first set are disposed in a first level providing first projected widths at an isocenter plane, and the leaves of the second set are disposed in a second level providing, at the isocenter plane, second projected widths that are substantially same as the corresponding first projected widths; and
    the leaves in the first level are arranged offset from the leaves in the second level in a direction generally traverse to the first and second directions such that one of the first projected widths offsets about half of corresponding one of the second projected widths at the isocenter.

7. The multileaf collimator of claim 6 wherein the leaves in the first and second sets substantially focus on a converging virtual point located substantially at a radiation source.

8. The multileaf collimator of claim 6 wherein the first projected widths at the isocenter plane are substantially identical and the second projected widths at the isocenter plane are substantially identical.

9. The multileaf collimator of claim 6 wherein the first projected widths at the isocenter plane are variable and the second projected widths at the isocenter plane are variable.

10. The multileaf collimator of claim 6 wherein a quantity of the leaves in the first set is different from a quantity of the leaves in the second set.

11. The multileaf collimator of claim 6 wherein a height of the leaves in the first level is different from a height of the leaves in the second level.

12. The multileaf collimator of claim 6 wherein the leaves in the first and second sets are supported by one or more movable carriages.

13. The multileaf collimator of claim 6 wherein the leaves in the first and second sets have a substantially trapezoidal cross section where the parallel sides of the trapezoidal cross-section have different dimensions.

14. The multileaf collimator of claim 6 wherein at least some of the leaves of the first set have an end portion having an upward and/or downward extended portion.

* * * * *